US012303704B2

(12) United States Patent
Snyder et al.

(10) Patent No.: US 12,303,704 B2
(45) Date of Patent: May 20, 2025

(54) WATER-RESISTANT ELECTROCARDIOGRAM SENSOR ASSEMBLY FOR A WEARABLE MEDICAL DEVICE

(71) Applicant: ZOLL MEDICAL CORPORATION, Chelmsford, MA (US)

(72) Inventors: Brian D. Snyder, Pittsburgh, PA (US); Gordon A. Slippy, Murrysville, PA (US); Richard S. Sharbaugh, New Kensington, PA (US); Andrew R. Bigham, Pittsburgh, PA (US); Christopher S. Lucci, Murrysville, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 321 days.

(21) Appl. No.: 17/810,724

(22) Filed: Jul. 5, 2022

(65) Prior Publication Data
US 2023/0052388 A1   Feb. 16, 2023

Related U.S. Application Data

(60) Provisional application No. 63/230,351, filed on Aug. 6, 2021.

(51) Int. Cl.
*A61N 1/39* (2006.01)
(52) U.S. Cl.
CPC ............. *A61N 1/3931* (2013.01); *A61N 1/39* (2013.01)

(58) Field of Classification Search
CPC .................... A61N 1/3931; A61N 1/39; A61B 2560/0443; A61B 5/6804; A61B 5/28
See application file for complete search history.

(56) References Cited

U.S. PATENT DOCUMENTS

| | | | |
|---|---|---|---|
| 10,463,867 B2 | 11/2019 | Kaib et al. | |
| 11,259,580 B2* | 3/2022 | Young | A61B 5/01 |
| 2003/0004547 A1 | 1/2003 | Owen et al. | |
| 2006/0161205 A1* | 7/2006 | Mitrani | A61N 1/3702 607/4 |
| 2011/0160601 A1 | 6/2011 | Wang et al. | |
| 2011/0286173 A1* | 11/2011 | Moore | G11B 33/08 29/458 |
| 2013/0325096 A1* | 12/2013 | Dupelle | A61N 1/0496 607/142 |
| 2017/0056682 A1 | 3/2017 | Kumar et al. | |
| 2017/0258402 A1* | 9/2017 | Acquista | H01R 31/00 |

(Continued)

OTHER PUBLICATIONS

IS/IEC 60529 (2001): Degrees of protection provided by enclosures (IP Code) [ETD 1: Basic Electrotechnical Standards] (Year: 2001).*

(Continued)

*Primary Examiner* — Catherine M Voorhees
(74) *Attorney, Agent, or Firm* — Finch & Maloney PLLC

(57) ABSTRACT

A waterproof modular electrocardiogram (ECG) electrode assembly for use in a wearable cardiac monitoring device comprises a first, main circuit board comprising active ECG processing circuitry encapsulated in a waterproof moldable dielectric polymer, and an ECG electrode mechanically coupled to the waterproof moldable dielectric polymer, the ECG electrode configured to be electrically coupled to a portion of the main circuit board.

19 Claims, 14 Drawing Sheets

(56) References Cited

U.S. PATENT DOCUMENTS

2019/0029599 A1   1/2019  Golda et al.
2020/0101278 A1*  4/2020  Freeman .............. A61N 1/3625
2022/0082236 A1*  3/2022  St.Ives ................... F21V 21/40
2023/0031279 A1*  2/2023  Chahine ................... D01F 1/09

OTHER PUBLICATIONS

International Search Report and Written Opinion from corresponding International Application No. PCT/US2022/038670 dated Nov. 18, 2022.

* cited by examiner

WATER-RESISTANT ELECTROCARDIOGRAM SENSOR ASSEMBLY FOR A WEARABLE MEDICAL DEVICE

CROSS-REFERENCE TO RELATED APPLICATIONS

This application claims priority under 35 U.S.C. § 119(e) to U.S. Provisional Patent application Ser. No. 63/230,351, titled "WATER-RESISTANT ELECTROCARDIOGRAM SENSOR ASSEMBLY FOR A WEARABLE MEDICAL DEVICE," filed Aug. 6, 2021, the entire contents of which is incorporated herein by reference for all purposes.

BACKGROUND

The present disclosure is generally directed to systems and methods of monitoring the cardiac activity of a subject.

There are a wide variety of electronic and mechanical devices for monitoring and treating subjects' medical conditions. In some examples, depending on the underlying medical condition being monitored or treated, medical devices such as cardiac monitors or defibrillators may be surgically implanted or externally connected to the subject. In some examples, physicians may use medical devices alone or in combination with drug therapies to treat conditions such as cardiac arrhythmias.

One of the deadliest cardiac arrhythmias is ventricular fibrillation, which occurs when normal, regular electrical impulses are replaced by irregular and rapid impulses, causing the heart muscle to stop normal contractions and to begin to quiver. Normal blood flow ceases, and organ damage or death can result in minutes if normal heart contractions are not restored. Because the victim has no perceptible warning of the impending fibrillation, death often occurs before the necessary medical assistance can arrive. Other cardiac arrhythmias can include excessively slow heart rates known as bradycardia or excessively fast heart rates known as tachycardia. Cardiac arrest can occur when a subject in which various arrhythmias of the heart, such as ventricular fibrillation, ventricular tachycardia, pulseless electrical activity (PEA), and asystole (e.g., heart stops all electrical activity) result in the heart providing insufficient levels of blood flow to the brain and other vital organs for the support of life.

Cardiac arrest and other cardiac health ailments are a major cause of death worldwide. Various resuscitation efforts aim to maintain the body's circulatory and respiratory systems during cardiac arrest in an attempt to save the life of the subject. The sooner these resuscitation efforts begin, the better the subject's chances of survival. Implantable cardioverter/defibrillators (ICDs) or external defibrillators (such as manual defibrillators or automated external defibrillators (AEDs)) have significantly improved the ability to treat these otherwise life-threatening conditions. Such devices operate by applying corrective electrical pulses directly to the subject's heart. Ventricular fibrillation or ventricular tachycardia can be treated by an implanted or external defibrillator, for example, by providing a therapeutic shock to the heart in an attempt to restore normal rhythm. To treat conditions such as bradycardia, an implanted or external pacing device can provide pacing stimuli to the subject's heart until intrinsic cardiac electrical activity returns.

Example external cardiac monitoring and/or treatment devices include cardiac monitors, the ZOLL LifeVest® wearable cardioverter defibrillator available from ZOLL Medical Corporation, and the AED Plus™ also available from ZOLL Medical Corporation. In implementation, such devices need to be serviced and/or re-assembled on return to the factory.

SUMMARY

In accordance with one aspect, there is provided a waterproof modular electrocardiogram (ECG) electrode assembly for use in a wearable cardiac monitoring device. The assembly comprises a first, main circuit board comprising active ECG processing circuitry encapsulated in a waterproof moldable dielectric polymer, and an ECG electrode mechanically coupled to the waterproof moldable dielectric polymer, the ECG electrode configured to be electrically coupled to a portion of the main circuit board.

In some embodiments, a portion of the main circuit board is configured to extend outside of the waterproof moldable dielectric polymer, and wherein the ECG electrode is configured to be electrically coupled to the portion of the main circuit board.

In some embodiments, the active ECG processing circuitry encapsulated in the moldable dielectric polymer comprises the active ECG processing circuit potted in the moldable dielectric polymer.

In some embodiments, the active ECG processing circuitry encapsulated in the moldable dielectric polymer comprises the active ECG processing circuit overmolded in the moldable dielectric polymer.

In some embodiments, the ECG electrode is removably mechanically coupled to the first waterproof moldable dielectric polymer and removably electrically coupled to the main circuit board.

In some embodiments, the assembly further comprises a second, different interface circuit board potted in an interface circuit waterproof moldable dielectric polymer and removably electrically and mechanically coupled to the main circuit board.

In some embodiments, at least one of the waterproof moldable dielectric polymer or the interface circuit waterproof moldable dielectric polymer comprises a hot-melt adhesive.

In some embodiments, the interface circuit board is removably electrically coupled to the main circuit board with a set of plug-in male and female electrical connectors.

In some embodiments, the assembly further comprises a dielectric sealing compound disposed between the main circuit board and the interface circuit board.

In some embodiments, the dielectric sealing compound includes a dielectric grease disposed about an electrical connection between the main circuit board and the interface circuit board.

In some embodiments, the assembly further comprises a housing including an upper shell and a lower shell, a perimeter of the ECG electrode disposed between the upper shell and the main waterproof moldable dielectric polymer.

In some embodiments, the assembly further comprises a mounting pad including a hook pad disposed on a base, the hook pad configured to removably secure the assembly within a garment of the wearable cardiac monitoring device by engaging complementary fasteners disposed in the garment, the base being removably rotatably securable to the lower shell.

In some embodiments, the base includes retention flanges configured to slide under portico features of the lower shell and locking tabs configured to removably engage slots defined in the lower shell between the portico features and secure the mounting pad in place in the lower shell.

In some embodiments, the upper shell is removably secured to the lower shell.

In some embodiments, the main circuit board and the waterproof moldable dielectric polymer are disposed within the housing.

In some embodiments, the ECG electrode includes a raised central region and a lowered peripheral region, the lowered peripheral region configured to be disposed between the upper shell and the waterproof moldable dielectric polymer.

In some embodiments, the assembly further comprises a gasket disposed between the lowered peripheral region and the upper shell.

In some embodiments, the assembly further comprises a conductor electrically coupling the ECG electrode to the portion of the main circuit board extending outside of the waterproof moldable dielectric polymer.

In some embodiments, the conductor is electrically and mechanically coupled to the ECG electrode at the lower peripheral region.

In some embodiments, the assembly further comprises wiring electrically connected to the main circuit board within the waterproof moldable dielectric polymer.

In some embodiments, the wiring enclosed in a waterproof cable including a flex relief connector extending outward from an interface between the cable and the waterproof moldable dielectric polymer.

In some embodiments, the assembly further comprises a tensile anchoring restraint extending from inside the cable and mechanically coupled to the main circuit board.

In some embodiments, the tensile anchoring restraint comprises a non-conductive fiber that enables the wiring to withstand between about 15 pounds and about 100 pounds of tension without separating from the main circuit board.

In some embodiments, the tensile anchoring restraint is secured within a notch formed in the main circuit board.

In some embodiments, the assembly further comprises a gas discharge tube electrically coupled to the main circuit board within the waterproof moldable dielectric polymer and configured to protect the active circuitry from electrical damage from a defibrillation shock delivered to a person wearing the wearable cardiac monitoring device.

In some embodiments, the waterproof moldable dielectric polymer provides liquid ingress protection rating of at least one of IPX3, IPX4, IPX5, IPX6, IPX7, or IPX8 as specified in international standard EN 60529 (British BS EN 60529:1992, European IEC 60509:1989).

In some embodiments, the waterproof moldable dielectric polymer provides solid particle ingress protection rating of one of IP3X, IP4X, IP5X, or IP6X as specified in international standard EN 60529 (British BS EN 60529:1992, European IEC 60509:1989).

In some embodiments, the ECG electrode is removably coupled to the waterproof moldable dielectric polymer with an adhesive.

In some embodiments, the assembly further comprises an insulating material layer disposed between the ECG electrode and the waterproof moldable dielectric polymer.

In some embodiments, the active circuitry is configured to digitize an ECG signal from a person wearing the wearable cardiac monitoring device.

In some embodiments, the assembly is removably disposable within a garment of the wearable cardiac monitoring device.

In some embodiments, the assembly includes a portion that is permanently disposed within a garment of the wearable cardiac monitoring device.

In some embodiments, the portion includes an interface circuit board potted in an interface circuit waterproof moldable dielectric polymer and removably electrically and mechanically coupled to the main circuit board.

In some embodiments, the wearable cardiac monitoring device comprises a wearable cardioverter defibrillator.

BRIEF DESCRIPTION OF THE DRAWINGS

Various aspects of at least one example are discussed below with reference to the accompanying figures, which are not intended to be drawn to scale. The figures are included to provide an illustration and a further understanding of the various aspects and examples, and are incorporated in and constitute a part of this specification, but are not intended to limit the scope of the disclosure. The drawings, together with the remainder of the specification, serve to explain principles and operations of the described and claimed aspects and examples. In the figures, each identical or nearly identical component that is illustrated in various figures is represented by a like numeral. For purposes of clarity, not every component may be labeled in every figure.

DETAILED DESCRIPTION

Figure 1:
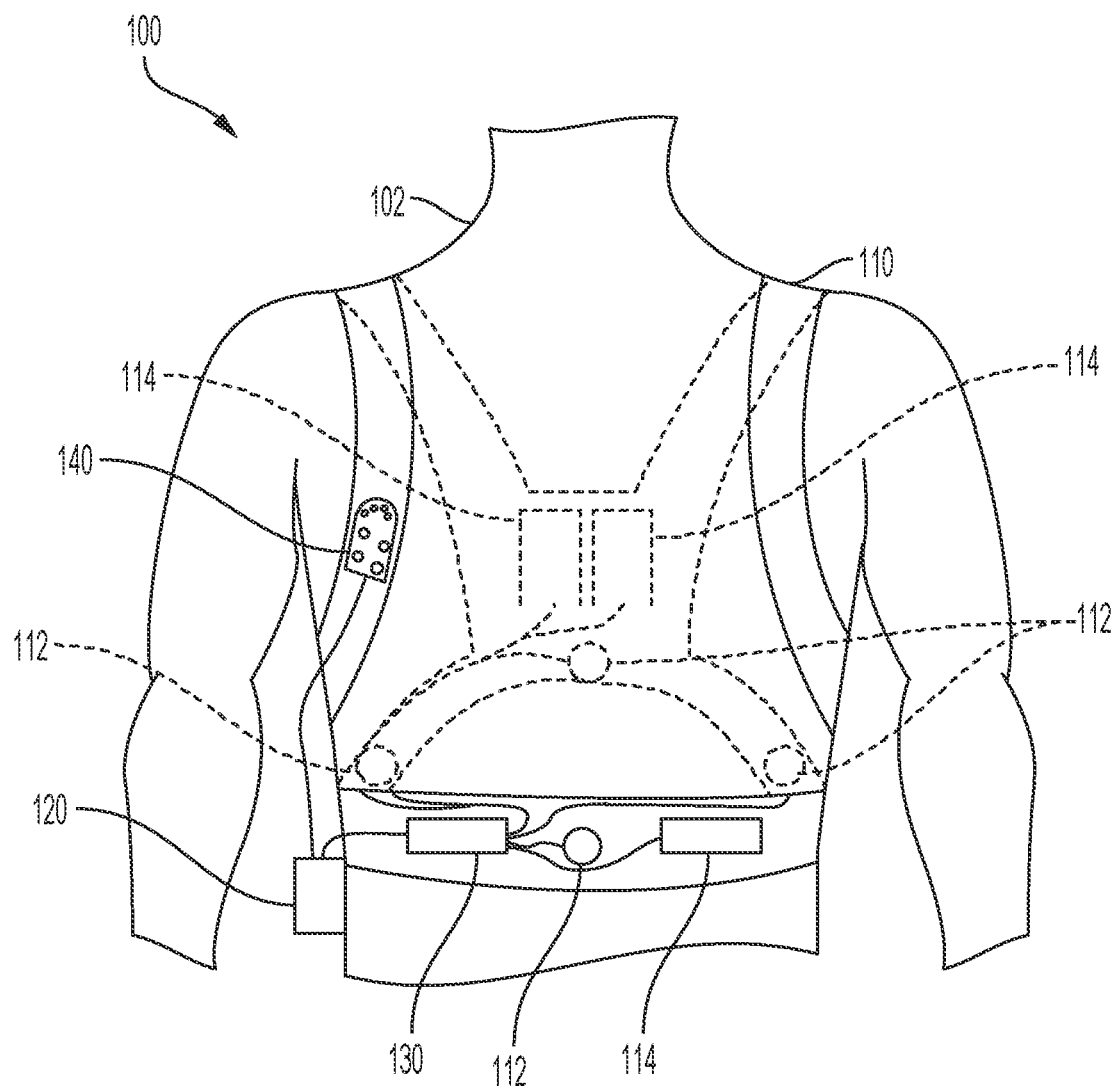
FIG. 1 depicts an example of a wearable medical device.

This disclosure relates to devices, systems and methods for monitoring cardiac activity of a subject.

Cardiac monitoring and/or treatment systems include electrocardiogram (ECG) sensing electrode assemblies that are used to measure electrical signals associated with the heart of a subject so that the systems can determine if the subject is exhibiting abnormal cardiac activity and may be in need of electrical therapy. Example devices, systems, and methods are described herein that provide for ECG electrodes that are water-resistant or waterproof and substantially immune or resistant to damage by ingress of particulate matter. The waterproof nature of the implementations disclosed herein provide for a subject to wear the therapeutic device system while bathing or showering. Such implementations allow for subjects to be protected in the event they experience a cardiac event while bathing or showering. Accordingly, aspects and examples disclosed herein include ECG electrode assemblies that are at least partially waterproof or in some instances sufficiently waterproof to be worn by a subject while bathing or showering to provide continuous ECG monitoring. ECG sensing electrodes in accordance with the disclosure herein are configured to be in contact with the patient's skin for continuous use and for extended periods of time. Examples of continuous use in the context of implementations herein are described further below. Similarly, examples of extended periods of time in the context of the implementations herein are also described below. During periods when the patient is protected from cardiac arrhythmias, the ECG electrode assemblies are continuously monitoring the patient's ECG signals for such arrhythmias for extended periods of time. In examples, such ECG electrodes are implemented as "dry" ECG electrodes and as such do not include hydrogel or other conductive ECG gel disposed between the electrode surface and the patient's skin. In examples, the ECG electrode can be a polarizable electrode. For example, as illustrated further below in connection with FIG. 1, the ECG electrodes described herein can be used for ambulatory cardiac monitoring and/or treatment devices, including wearable cardioverter defibrillators, cardiac holters, mobile cardiac telemetry and/or continuous event monitoring devices. In examples where the ECG electrodes are configured as "dry" electrodes, the ECG electrodes are more comfortable against the patient's skin for continuous use scenarios and/or extended wear durations, where such use is in the presence of high humidity and/or moisture. The assembly, disassembly, and maintenance of the device is convenient for the patient in such scenarios. Further, for the durations of the continuous use and/or extended periods of time as described herein, such ECG electrode assemblies allow for easy donning and removal of the device. In this regard, patients do not need to concern themselves with applying or re-applying conductive gel to the ECG electrodes before, during, or after physical activities, shower, or bathing. Implementations as described herein therefore confer the benefits of allowing for such ECG electrodes to be used in high humidity and/or wet environments.

Example devices, systems, and methods described herein are modular and allow for reuse of components of ECG electrode assemblies while also protecting such components in high humidity and/or wet environments. Such environments are characterized by, for example, humidity in excess of 65% (e.g., 65% to 100%, condensing or non-condensing) or in the presence of water and/or liquids at typical operating temperatures 32F to 131F (0C to 55C). For example, during use, a circuit board, wiring interface, or an electrode portion of an ECG electrode assembly may become damaged or may fail. In accordance with embodiments herein, the damaged or defective portions of the ECG electrode assembly may be replaced and the non-damaged or functional portions may be reused with the replaced components.

Aspects and examples disclosed herein thus provide advantages with respect to cost and with respect to the number of replacement parts a user or supplier may keep on hand to maintain the ECG electrode assemblies of a monitoring and/or therapy electrode system of a subject in usable or optimal condition.

As described above, the teachings of the present disclosure can be generally applied to external cardiac monitoring and/or treatment devices (e.g., devices that are not completely implanted within the subject's body and configured for monitoring and/or treating cardiac conditions in the patient). External cardiac monitoring and/or treatment devices can include, for example, ambulatory cardiac devices that are capable of and designed for moving with the subject as the subject goes about his or her daily routine. Example cardiac monitoring and/or treatment devices include wearable cardioverter defibrillators (WCDs), in-hospital cardioverter defibrillators, short-term wearable cardiac monitoring and/or therapeutic devices, mobile cardiac telemetry devices, and other similar wearable cardiac devices.

The wearable medical device includes modular waterproof components, including the ECG electrode assemblies as described herein, and are capable of continuous use by the subject. In some implementations, the continuous use can be substantially or nearly continuous in nature. That is, the wearable medical device may be continuously used, including while the subject bathes, except for sporadic periods during which the use temporarily ceases, for example, when the wearable medical device is removed for service or laundering. Such substantially or nearly continuous use as described herein may nonetheless qualify as continuous use. For example, the wearable medical device can be configured to be worn by a subject for as many as 24 hours a day. In some implementations, the subject may remove the wearable medical device for a short portion of the day (e.g., for service or cleaning).

Further, the wearable medical device can be configured as a long term or extended use medical device. Such devices can be configured to be used by the subject for an extended period of several days, weeks, months, or even years. In some examples, the wearable medical device can be used by a subject for an extended period of at least one week. In some examples, the wearable medical device can be used by a subject for an extended period of at least 30 days. In some examples, the wearable medical device can be used by a subject for an extended period of at least one month. In some examples, the wearable medical device can be used by a subject for an extended period of at least two months. In some examples, the wearable medical device can be used by a subject for an extended period of at least three months. In some examples, the wearable medical device can be used by a subject for an extended period of at least six months. In some examples, the wearable medical device can be used by a subject for an extended period of at least one year. In some implementations, the extended use can be uninterrupted until a physician or other caregiver provides specific instruction to the subject to stop use of the wearable medical device.

Regardless of the extended period of wear, the use of the wearable medical device can include continuous or nearly continuous wear by the subject as described above. For example, the continuous use can include continuous wear or attachment of the wearable medical device to the subject, e.g., through one or more of the ECG electrode assemblies as described herein, during both periods of monitoring and periods when the device may not be monitoring the subject but is otherwise still worn by or otherwise attached to the subject. The wearable medical device can be configured to continuously monitor the subject for cardiac-related information (e.g., electrocardiogram (ECG) information, including arrhythmia information, heart sounds or heart vibrations, etc.) and/or non-cardiac information (e.g., blood oxygen, the subject's temperature, glucose levels, tissue fluid levels, and/or lung sounds or vibrations). The wearable medical device can carry out its monitoring in periodic or aperiodic time intervals or times. For example, the monitoring during intervals or times can be triggered by a user action or another event.

FIG. 1 illustrates an example of a medical device 100 that is external, ambulatory, and wearable by a subject 102, and configured to implement one or more configurations described herein. For example, the medical device 100 can be a non-invasive medical device configured to be located substantially external to the subject. Such a medical device 100 can be, for example, an ambulatory medical device that is capable of and designed for moving with the subject as the subject goes about his or her daily routine. For example, the medical device 100 as described herein can be bodily-attached to the subject such as the LifeVest® wearable cardioverter defibrillator available from ZOLL® Medical Corporation. In one example scenario, such wearable defibrillators can be worn nearly continuously or substantially continuously for two to three months at a time. During the period of time in which it is worn by the subject, the wearable defibrillator can be configured to continuously or substantially continuously monitor the vital signs of the subject and, upon determination that treatment is required, can be configured to deliver one or more therapeutic electrical pulses to the subject. For example, such therapeutic shocks can be pacing, defibrillation, cardioversion, or transcutaneous electrical nerve stimulation (TENS) pulses.

The medical device 100 can include one or more of the following: a garment 110, one or more sensing electrodes 112 (e.g., ECG electrodes), one or more therapy electrodes 114, a medical device controller 120, a connection pod 130, a subject interface pod 140, a belt, or any combination of these. In some examples, at least some of the components of the medical device 100 can be configured to be affixed to the garment 110 (or in some examples, permanently integrated into the garment 110), which can be worn about the subject's torso.

The medical device controller 120 can be operatively coupled to the sensing electrodes 112, which can be affixed to the garment 110, e.g., assembled into the garment 110 or removably attached to the garment, e.g., using hook and loop fasteners. In some implementations, the sensing electrodes 112 can be permanently integrated into the garment 110. The medical device controller 120 can be operatively coupled to the therapy electrodes 114. For example, the therapy electrodes 114 can also be assembled into the garment 110, or, in some implementations, the therapy electrodes 114 can be permanently integrated into the garment 110.

Component configurations other than those shown in FIG. 1 are possible. For example, the sensing electrodes 112 can be configured to be attached at various positions about the body of the subject 102. The sensing electrodes 112 can be operatively coupled to the medical device controller 120 through the connection pod 130. In some implementations, the sensing electrodes 112 can be adhesively attached to the subject 102. In some implementations, the sensing electrodes 112 and at least one of the therapy electrodes 114 can be included on a single integrated patch and adhesively applied to the subject's body.

The sensing electrodes 112 can be configured to detect surface electrical activity of the subject such as electrocardiogram (ECG) signals. In certain implementations, the sensing electrodes 112 can be associated with additional components disposed within a housing of the sensing electrode 112, such as accelerometers, acoustic signal detecting devices, and other measuring devices for recording additional physiological, motion, or posture parameters. For example, such additional components can also be configured to detect other types of subject physiological parameters and acoustic signals, such as tissue fluid levels, heart vibrations, lung vibrations, respiration vibrations, subject movement, etc. Example sensing electrodes 112 include a metal electrode with an oxide coating such as tantalum pentoxide electrodes, as described in, for example, U.S. Pat. No. 6,253,099 titled "Cardiac Monitoring Electrode Apparatus and Method," the content of which is incorporated herein by reference.

In some examples, the therapy electrodes 114 can also be associated with additional components disposed on the substrate of a therapy electrode 114, and such additional components can include sensors configured to detect ECG signals as well as other physiological signals of the subject similar to those described above.

The connection pod 130 can, in some examples, include a signal processor configured to amplify, filter, and digitize the cardiac signals prior to transmitting the cardiac signals to the medical device controller 120. In other examples, the sensing electrodes 112 may include ECG electrode assemblies having circuitry configured to digitize the cardiac signals prior to transmitting the cardiac signals to the medical device controller 120.

One or more of the therapy electrodes 114 can be configured to deliver one or more therapeutic defibrillating shocks to the body of the subject 102 when the medical device 100 determines that such treatment is warranted based on the signals detected by the sensing electrodes 112 and processed by the medical device controller 120. Example therapy electrodes 114 can include conductive metal electrodes such as stainless-steel electrodes that include, in certain implementations, one or more conductive gel deployment devices configured to deliver conductive gel to the metal electrode prior to delivery of a therapeutic shock.

In some implementations, medical devices as described herein can be configured to switch between a therapeutic medical device and a monitoring medical device that is configured to only monitor a subject (e.g., not provide or perform any therapeutic functions). For example, therapeutic components such as the therapy electrodes 114 and associated circuitry can be optionally decoupled from (or coupled to) or switched out of (or switched in to) the medical device. For example, a medical device can have optional therapeutic elements (e.g., defibrillation and/or pacing electrodes, components, and associated circuitry) that are configured to operate in a therapeutic mode. The optional therapeutic elements can be physically decoupled from the medical device to convert the therapeutic medical device into a monitoring medical device for a specific use (e.g., for operating in a monitoring-only mode) or a subject.

Alternatively, the optional therapeutic elements can be deactivated (e.g., by a physical or a software switch), essentially rendering the therapeutic medical device a monitoring medical device for a specific physiologic purpose or a particular subject. As an example of a software switch, an authorized person can access a protected user interface of the medical device and select a preconfigured option or perform some other user action via the user interface to deactivate the therapeutic elements of the medical device.

Figure 2A:
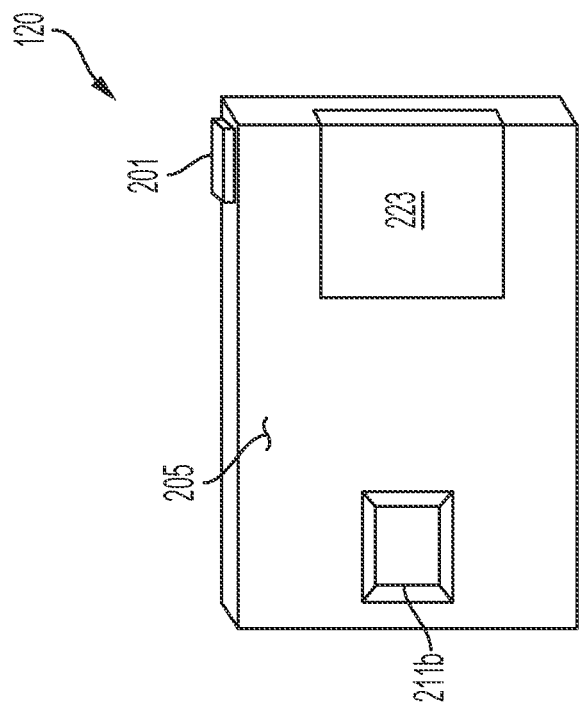
FIG. 2A depicts a first view of a medical device controller for the wearable medical device of FIG. 1.
Figure 2B:
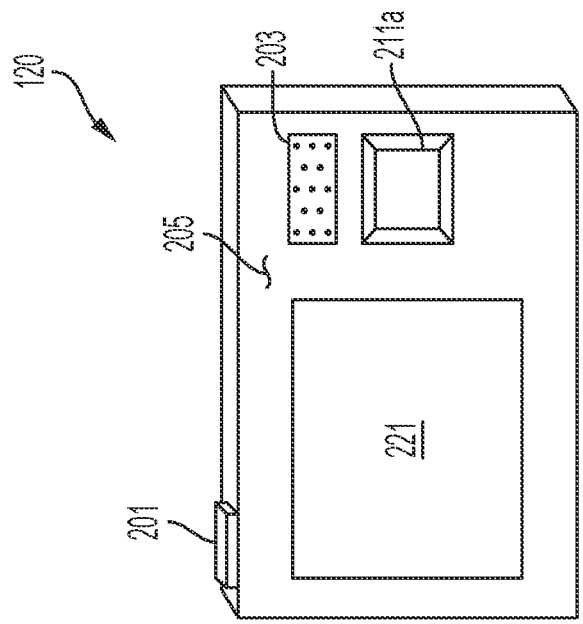
FIG. 2B depicts a second view of a medical device controller for the wearable medical device of FIG. 1.

FIGS. 2A and 2B illustrate an example medical device controller 120. For example, the controller 120 includes a connector receptacle 201 for connecting the sensing and/or therapy electrode components to the controller 120. The controller 120 includes a speaker 203 for providing audio prompts to the subject and/or a bystander. The controller 120 includes circuitry as further described below with reference to FIG. 2C. The circuitry is housed within a mechanical housing structure 205 to protect the circuitry and other internal components of the controller 120 from physical damage, particle ingress, and/or water ingress. The controller includes one or more response buttons 211a, 211b. A subject wearing the wearable medical device can communicate with the controller 120 via the buttons 211a, 211b. For example, if the device detects a life-threatening arrhythmia condition in the subject, the controller 120 can direct the subject to press the one or more buttons 211a, 211b. In some examples, the controller 120 can include a display screen 221. For example, the display screen 221 can be a touch-sensitive panel screen responsive to subject input in the form of touch or physical force applied to the screen. For example, the display screen 221 can display controls and/or prompts to the subject and is responsive to the subject's touch or application of physical force on the displayed controls. The controller 120 can be powered by a removable battery 210 (see FIG. 2C below) that is housed within a battery chamber 223.

Figure 2C:
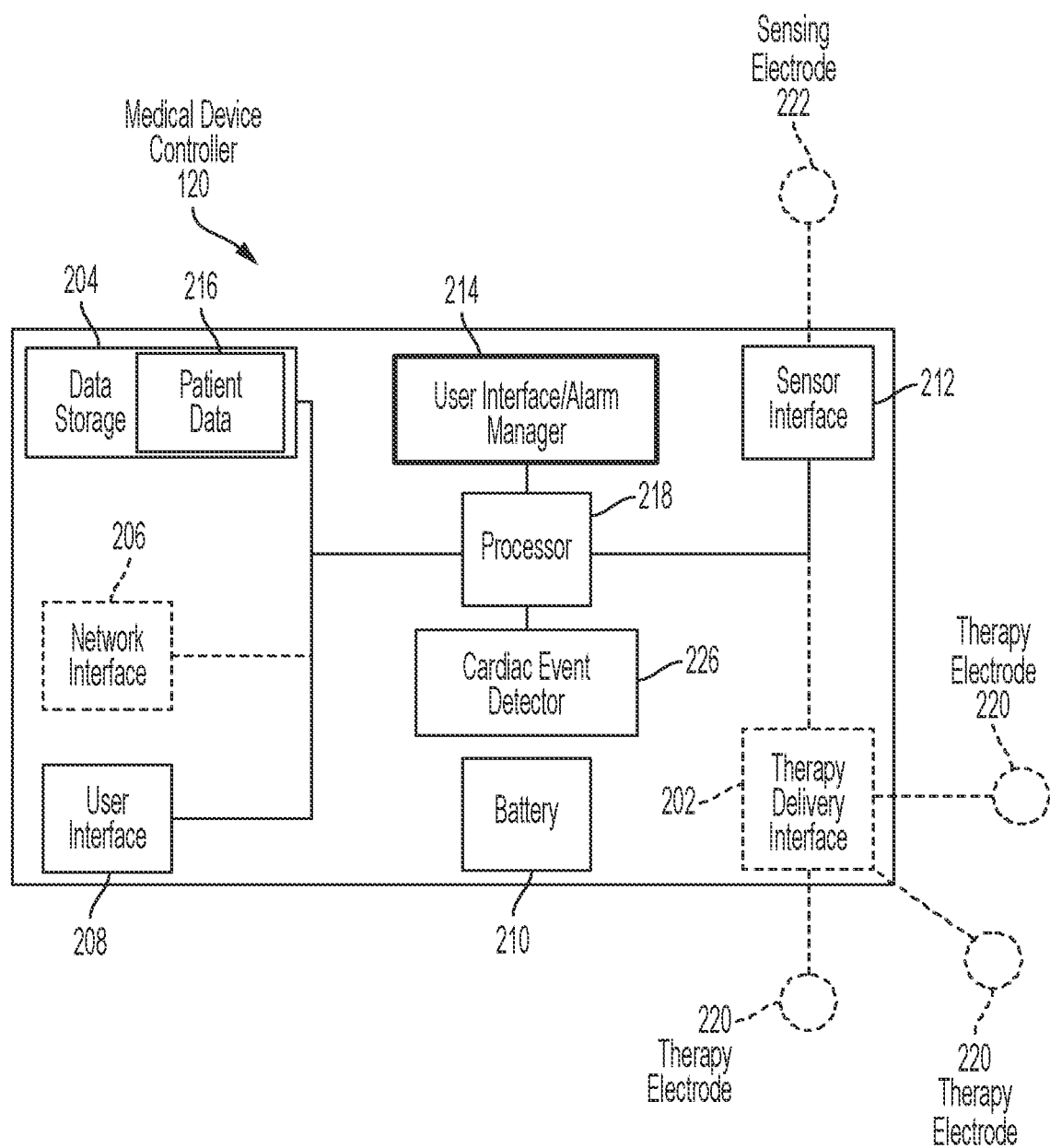
FIG. 2C depicts a component-level view of an example of a medical device controller for the wearable medical device of FIG. 1.

FIG. 2C illustrates a sample component-level view of the medical device controller 120 of the medical device 100 of FIG. 1. As shown in FIG. 2C, the medical device controller 120 can include a therapy delivery interface circuit 202, a data storage 204, a network interface 206, a user interface 208, at least one battery 210, a sensor interface 212, a user interface/alarm manager 214, and least one processor 218.

The therapy delivery interface circuit 202 can be coupled to one or more electrodes 220 configured to provide therapy to the subject (e.g., therapy electrodes 114 as described above in connection with FIG. 1). For example, the therapy delivery interface circuit 202 can include, or be operably connected to, circuitry components that are configured to generate and provide the therapeutic shock. The circuitry components can include, for example, resistors, capacitors, relays and/or switches, electrical bridges such as an H-bridge (e.g., including a plurality of insulated gate bipolar transistors or IGBTs), voltage and/or current measuring components, and other similar circuitry components arranged and connected such that the circuitry components work in concert with the therapy delivery circuit and under control of one or more processors (e.g., processor 218) to provide, for example, one or more pacing or defibrillation therapeutic pulses.

Pacing pulses can be used to treat cardiac arrhythmias such as bradycardia (e.g., less than 30 beats per minute) and tachycardia (e.g., more than 150 beats per minute) using, for example, fixed rate pacing, demand pacing, anti-tachycardia pacing, and the like. Defibrillation pulses can be used to treat ventricular tachycardia and/or ventricular fibrillation.

The capacitors of the therapy delivery interface 202 can include a parallel-connected capacitor bank consisting of a plurality of capacitors (e.g., two, three, four or more capacitors). These capacitors can be switched into a series connection during discharge for a defibrillation pulse. For example, four capacitors of approximately 650 uF can be used. The capacitors can have between 350 to 500 volt surge rating and can be charged in approximately 15 to 30 seconds from a battery pack. In other embodiments, a single capacitor can be used, or a plurality of capacitors that are electrically connected in parallel or in series may be utilized.

For example, each defibrillation pulse can deliver between 60 to 180 joules of energy. In some implementations, the defibrillating pulse can be a biphasic truncated exponential waveform, whereby the signal can switch between a positive and a negative portion (e.g., charge directions). This type of waveform can be effective at defibrillating subjects at lower energy levels when compared to other types of defibrillation pulses (e.g., such as monophasic pulses). For example, an amplitude and a width of the two phases of the energy waveform can be automatically adjusted to deliver a precise energy amount (e.g., 150 joules) regardless of the subject's body impedance. The therapy delivery interface circuit 202 can be configured to perform the switching and pulse delivery operations, e.g., under control of the processor 218. As the energy is delivered to the subject, the amount of energy being delivered can be tracked. For example, the amount of energy can be kept to a predetermined constant value even as the pulse waveform is dynamically controlled based on factors such as the body impedance of the subject to which the pulse is being delivered.

The data storage 204 can include one or more of non-transitory computer readable media, such as flash memory, solid state memory, magnetic memory, optical memory, cache memory, combinations thereof, and others. The data storage 204 can be configured to store executable instructions and data used for operation of the medical device controller 120. In certain implementations, the data storage can include executable instructions that, when executed, are configured to cause the at least one processor 218 to perform one or more functions.

In some examples, the network interface 206 can facilitate the communication of information between the medical device controller 120 and one or more other devices or entities over a communications network. For example, where the medical device controller 120 is included in an ambulatory medical device (such as medical device 100), the network interface 206 can be configured to communicate with a remote computing device such as a remote server or other similar computing device. The network interface 206 can include communications circuitry for transmitting data in accordance with a Bluetooth® wireless standard for exchanging such data over short distances to an intermediary device(s) (e.g., a base station, a "hotspot" device, a smartphone, a tablet, a portable computing device, and/or other devices in proximity of the wearable medical device 100). The intermediary device(s) may in turn communicate the data to a remote server over a broadband cellular network communications link. The communications link may implement broadband cellular technology (e.g., 2.5G, 2.75G, 3G, 4G, 5G cellular standards) and/or Long-Term Evolution (LTE) technology or GSM/EDGE and UMTS/HSPA technologies for high-speed wireless communication. In some implementations, the intermediary device(s) may communicate with a remote server over a Wi-Fi™ communications link based on the IEEE 802.11 standard.

In certain implementations, the user interface 208 can include one or more physical interface devices such as input devices, output devices, and combination input/output devices and a software stack configured to drive operation of the devices. These user interface elements may render visual, audio, and/or tactile content. Thus, the user interface 208 may receive input or provide output, thereby enabling a user to interact with the medical device controller 120.

The medical device controller 120 can also include at least one battery 210 configured to provide power to one or more components integrated in the medical device controller 120. The battery 210 can include a rechargeable multi-cell battery pack. In one example implementation, the battery 210 can include three or more 2200 mAh lithium ion cells that provide electrical power to the other device components within the medical device controller 120. For example, the battery 210 can provide its power output in a range of between 20 mA to 1,000 mA (e.g., 40 mA) output and can support 24 hours, 48 hours, 72 hours, or more, of runtime between charges. In certain implementations, the battery capacity, runtime, and type (e.g., lithium ion, nickel-cadmium, or nickel-metal hydride) can be changed to best fit the specific application of the medical device controller 120.

The sensor interface 212 can be coupled to one or more sensors configured to monitor one or more physiological parameters of the subject. As shown, the sensors may be coupled to the medical device controller 120 via a wired or wireless connection. The sensors can include one or more electrocardiogram (ECG) electrodes 222 (e.g., similar to sensing electrodes 112 as described above in connection with FIG. 1).

The ECG electrodes 222 can monitor a subject's ECG information. For example, the ECG electrodes 222 can be galvanic (e.g., conductive) and/or capacitive electrodes configured to measure changes in a subject's electrophysiology to measure the subject's ECG information. The ECG electrodes 222 can transmit information descriptive of the ECG signals to the sensor interface 212 for subsequent analysis.

The sensor interface 212 can be coupled to any one or combination of sensing electrodes/other sensors to receive other subject data indicative of subject parameters. Once data from the sensors has been received by the sensor interface 212, the data can be directed by the at least one processor 218 to an appropriate component within the medical device controller 120. For example, if ECG data is collected by sensing electrode 222 and transmitted to the sensor interface 212, the sensor interface 212 can transmit the data to the at least one processor 218 which, in turn, relays the data to a cardiac event detector 226. The cardiac event data can also be stored as patient data 216 on the data storage 204.

In certain implementations, the user interface/alarm manager 214 can be configured to manage alarm profiles and notify one or more intended recipients of events specified within the alarm profiles as being of interest to the intended recipients. These intended recipients can include external entities such as users (subjects, physicians, and monitoring personnel) as well as computer systems (monitoring systems or emergency response systems). The user interface/alarm manager 214 can be implemented using hardware or a combination of hardware and software. For instance, in some examples, the user interface/alarm manager 214 can be implemented as a software component that is stored within the data storage 204 and executed by the at least one processor 218. In this example, the instructions included in the alarm manager 214 can cause the at least one processor 218 to configure alarm profiles and notify intended recipients using the alarm profiles. In other examples, alarm manager 214 can be an application-specific integrated circuit (ASIC) that is coupled to the at least one processor 218 and configured to manage alarm profiles and notify intended recipients using alarms specified within the alarm profiles. Thus, examples of alarm manager 214 are not limited to a particular hardware or software implementation.

In some implementations, the at least one processor 218 includes one or more processors (or one or more processor cores) that each are configured to perform a series of instructions that result in manipulated data and/or control the operation of the other components of the medical device controller 120. In some implementations, when executing a specific process (e.g., cardiac monitoring), the at least one processor 218 can be configured to make specific logic-based determinations based on input data received, and be further configured to provide one or more outputs that can be used to control or otherwise inform subsequent processing to be carried out by the at least one processor 218 and/or other processors or circuitry with which the at least one processor 218 is communicatively coupled. Thus, the at least one processor 218 reacts to specific input stimulus in a specific way and generates a corresponding output based on that input stimulus. In some examples, the at least one processor 218 can proceed through a sequence of logical transitions in which various internal register states and/or other bit cell states internal or external to the at least one processor 218 may be set to logic high or logic low. As referred to herein, the at least one processor 218 can be configured to execute a function where software is stored in a data store coupled to the at least one processor 218, the software being configured to cause the at least one processor 218 to proceed through a sequence of various logic decisions that result in the function being executed. The various components that are described herein as being executable by the at least one processor 218 can be implemented in various forms of specialized hardware, software, or a combination thereof. For example, the processor can be a digital signal processor (DSP) such as a 24-bit DSP processor. The at least one processor can be or include a multi-core processor, e.g., having two or more processing cores. The processor can be an Advanced RISC Machine (ARM) processor such as a 32-bit ARM processor. The at least one processor can execute an embedded operating system, and include services provided by the operating system that can be used for file system manipulation, display and audio generation, basic networking, firewalling, data encryption and communications.

Figure 3:
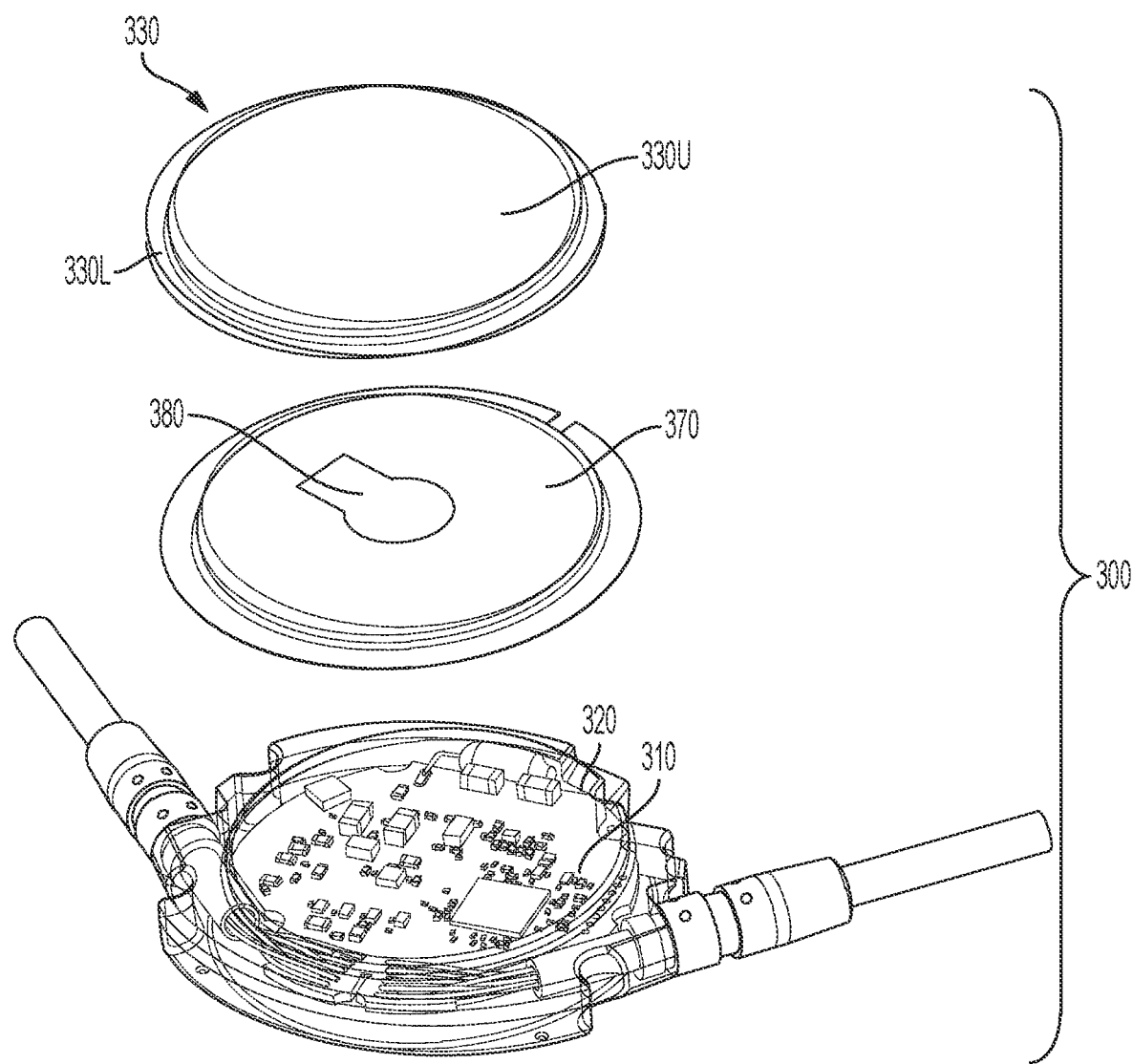
FIG. 3 is an exploded view of portions of an example of a water-resistant electrocardiogram (ECG) electrode assembly.

Several components of one example of a waterproof modular electrocardiogram (ECG) electrode assembly for use in a wearable medical device, for example, a cardiac monitoring device/defibrillator are illustrated in an exploded view in FIG. 3, are indicated generally at 300. The ECG electrode assembly 300 may be removably disposed within a garment 110 of a wearable cardiac monitoring device/defibrillator, or may include one or more portions that are permanently secured within the garment 110, for example, an interface circuit board 390 (FIG. 6) and associated waterproof moldable dielectric polymer, cables, and wiring as described below. The ECG electrode assembly 300 includes a first, main circuit board 310 comprising active ECG processing circuitry potted in a main waterproof moldable dielectric polymer 320. The active ECG processing circuitry is configured to digitize an ECG signal from a person wearing a wearable cardiac monitoring device/defibrillator in which the ECG electrode assembly 300 is installed. The ECG electrode assembly 300 further includes an ECG electrode 330, illustrated as disconnected from the main waterproof moldable dielectric polymer 320 in the exploded view of FIG. 3, but configured to be removably mechanically coupled to the main waterproof moldable dielectric polymer 320. The ECG electrode 330 may comprise or consist or tantalum or any other suitable electrode material.

In some embodiments, some circuit components of the ECG electrode assembly 300, for example, one or more circuit elements or nodes on the main circuit board 310 may include high impedance elements. In implementations, to eliminate or reduce potential for leakage current to pass through the waterproof moldable dielectric polymer 320, a cover can be disposed over one or more high impedance circuit elements or nodes. In examples, the cover includes a plastic material cover. Additionally or alternatively, a metal-based guard ring (e.g., a driven guard ring) can be disposed about the one or more high impedance circuit elements or nodes. For example, a high voltage circuit track may be surrounded by, e.g., "FR4" PCB material, and a driven guard ring disposed further about the PCB material. In examples, the driven guard ring can be at a same or similar electrical potential as the circuit track.

Additionally or alternatively, in implementations, a recess can be disposed in the waterproof moldable dielectric polymer 320 over the one or more high impedance circuit elements or nodes to prevent leakage current from passing through the waterproof moldable dielectric polymer 320 between terminals of the high impedance circuit elements or nodes. In this manner, the recess introduces an air gap or other inert gas in order to prevent the leakage current.

Figure 4:
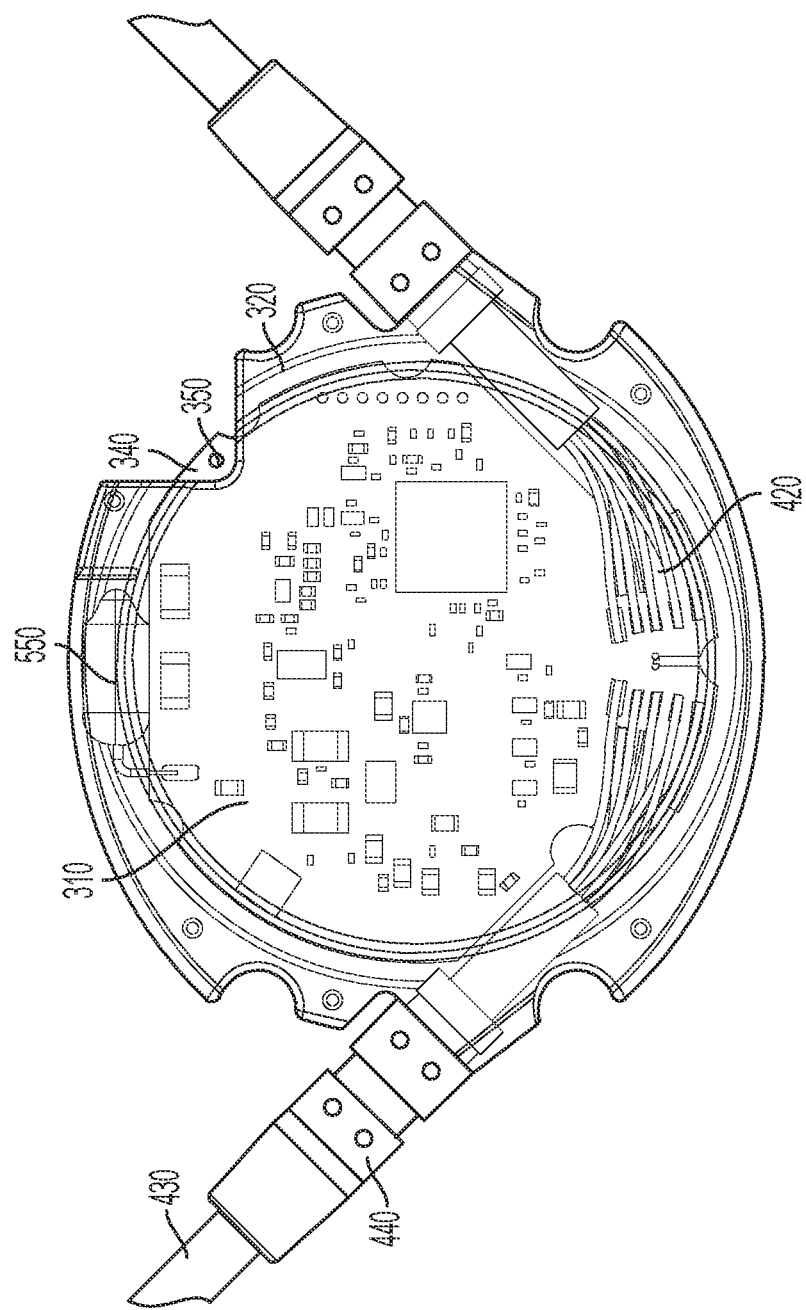
FIG. 4 depicts an example of a first, main circuit board assembly and associated moldable dielectric polymers and electrical connections for an ECG electrode assembly.

The ECG electrode 330 is further configured to be electrically coupled to a portion 340 (FIG. 4) of the main circuit board 310 extending outside of the main waterproof moldable dielectric polymer 320. As illustrated in FIG. 4, the portion 340 of the main circuit board 310 extending outside of the main waterproof moldable dielectric polymer 320 to which the ECG electrode 330 electrically connects may include a contact or aperture 350 to receive a first end of a conductor 360 (for example, a wire), illustrated in FIGS. 5, 6, and 8 that is electrically connected on its second end to the ECG electrode 330. The ECG electrode 330 may be removably electrically coupled to the main circuit board 310 by a meltable solder joint electrically connecting the conductor 360 to the contact or aperture 350 or to the ECG electrode 330.

Referring back to FIG. 3, in some examples, an electrical insulator 370 formed of, for example, mylar may be disposed between the ECG electrode 330 and the main waterproof moldable dielectric polymer 320. Pressure sensitive adhesive 380 disposed on upper and lower surfaces of the electrical insulator 370 may facilitate removably mechanically securing the ECG electrode 330 to the main waterproof moldable dielectric polymer 320.

In some examples, the main waterproof moldable dielectric polymer 320 may be formed of or include a waterproof thermoplastic material. In some examples, the main waterproof moldable dielectric polymer 320 may be formed of or include a hotmelt adhesive material. In some examples, the main waterproof moldable dielectric polymer 320 may include or consist of one of the Henkel LOCTITE® TECHNOMELT® polyamide or polyolefin thermoplastic materials, for example, TECHNOMELT® PA 6208 polyamide hotmelt adhesive. Example encapsulation techniques are described in further detail below.

Figure 6:
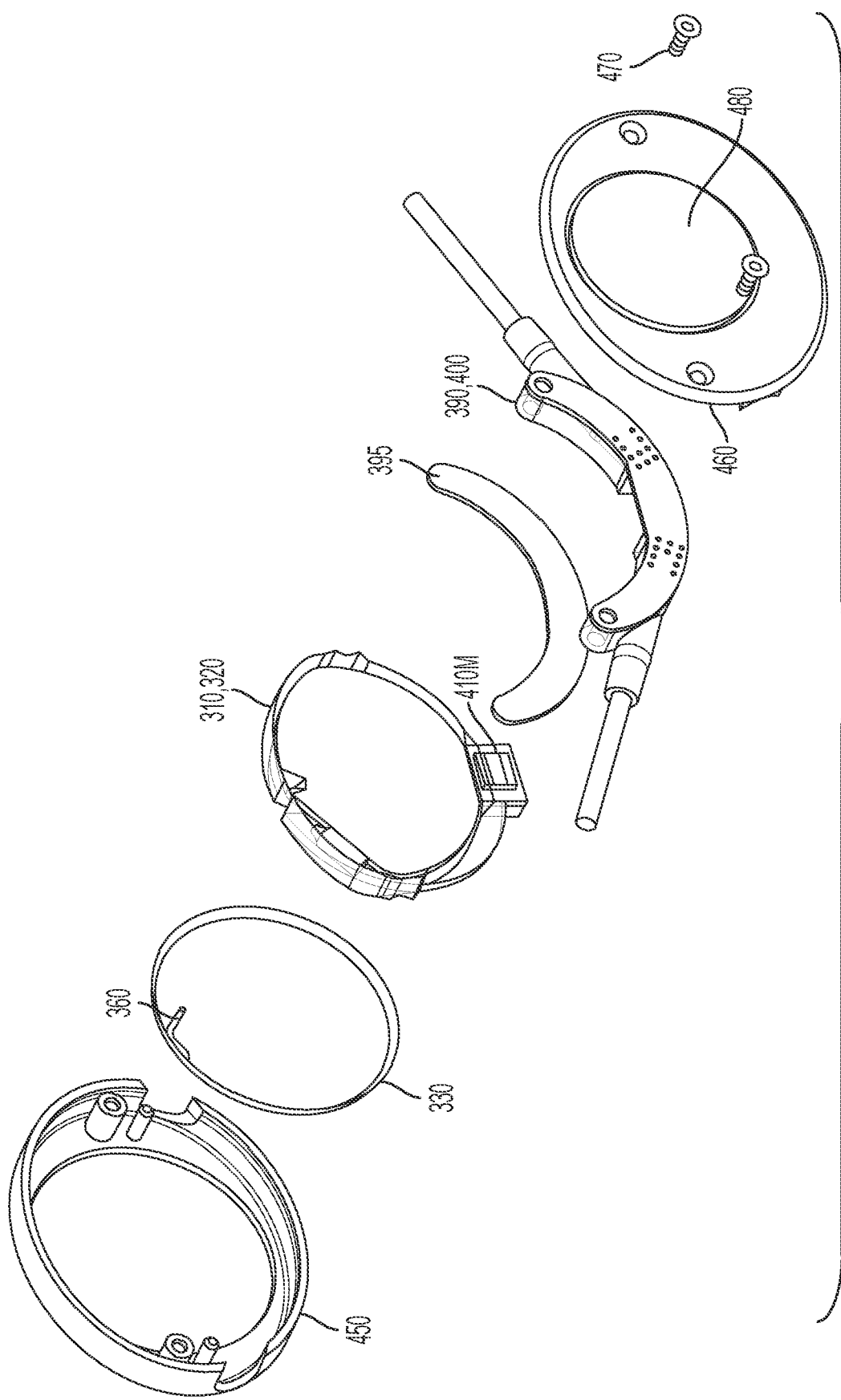
FIG. 6 is an exploded view of portions of an example of a water-resistant ECG electrode assembly.
Figure 7:
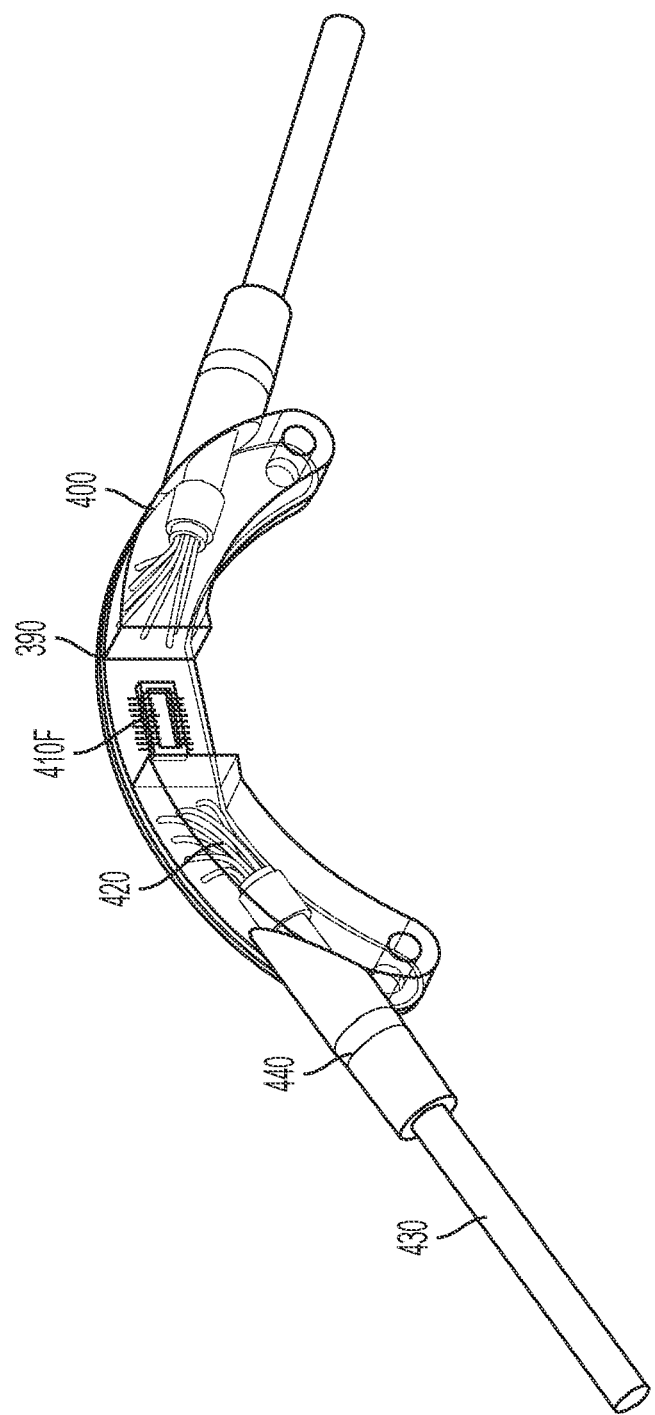
FIG. 7 illustrates an example of a wiring interface circuit board of an example of a water-resistant ECG electrode assembly.

In some examples, the electrode assembly 300 includes a second, interface circuit board 390 encapsulated in an interface circuit waterproof moldable dielectric polymer 400, as illustrated in FIGS. 6 and 7. The interface circuit board 390 may be removably electrically and mechanically coupled to the main circuit board 310. The interface circuit waterproof moldable dielectric polymer 400 may be formed of a same or similar material as the main waterproof moldable dielectric polymer 320. The interface circuit board 390 may be removably electrically coupled to the main circuit board 310 with a set of plug-in male and female electrical connectors 410M, 410F. The electrical connector 410M of the main circuit board 310 is illustrated in FIG. 6. In some examples, the male connectors 410M are on the main circuit board 310 and the female connectors 410F are on the interface circuit board 390, and in other examples, the male connectors 410M are on the interface circuit board 390 and the female connectors 410F are on the main circuit board 310. In some examples, a dielectric sealing compound is disposed between the waterproof moldable dielectric polymer 320 containing the main circuit board 310 and the interface circuit waterproof moldable dielectric polymer 400 containing the interface circuit board 390 to reduce or prevent ingress of water or particulate matter into the interface between the circuit boards or electrical connectors. The dielectric sealing compound may include a dielectric grease 395. For example, the grease comprises a silicone-based grease that repels moisture and protects electrical connections against corrosion. The interface circuit board 390 is used to couple to wiring 420 included in and extending from ends of waterproof cables 430 that interface with the interface circuit waterproof moldable dielectric polymer 400 by flex relief connectors 440. In some examples, two cables 430 connect to the interface circuit board 390, one to carry signals to a monitor/controller 120 of the wearable medical device 100 in which the ECG electrode assembly 300 is installed, and another to receive signals from another ECG electrode assembly 300 and pass these signals on to the monitor/controller 120. If an ECG electrode assembly 300 is last in a series of electrically connected ECG electrode assemblies 300, the interface circuit board 390 may receive only a single cable 430 to carry signals back to the monitor/controller 120.

In other examples, the ECG electrode assembly 300 does not include a separate interface circuit board 390, but rather the wiring 420, cables 430, and strain relief connectors 440 interface directly with the main circuit board 310 and main waterproof moldable dielectric polymer 320 as illustrated in FIGS. 3 and 4. As illustrated, the wiring 420 is connected to contacts on the main circuit board 310 within the main waterproof moldable dielectric polymer 320, for example, by soldering. The wiring 420 passes through the flex relief connectors 440 coupled to the main waterproof moldable dielectric polymer 320 and into the waterproof cables 430. The flex relief connectors 440 extend outward from interfaces between the waterproof cables 430 and the main waterproof moldable dielectric polymer 320.

Figure 5:
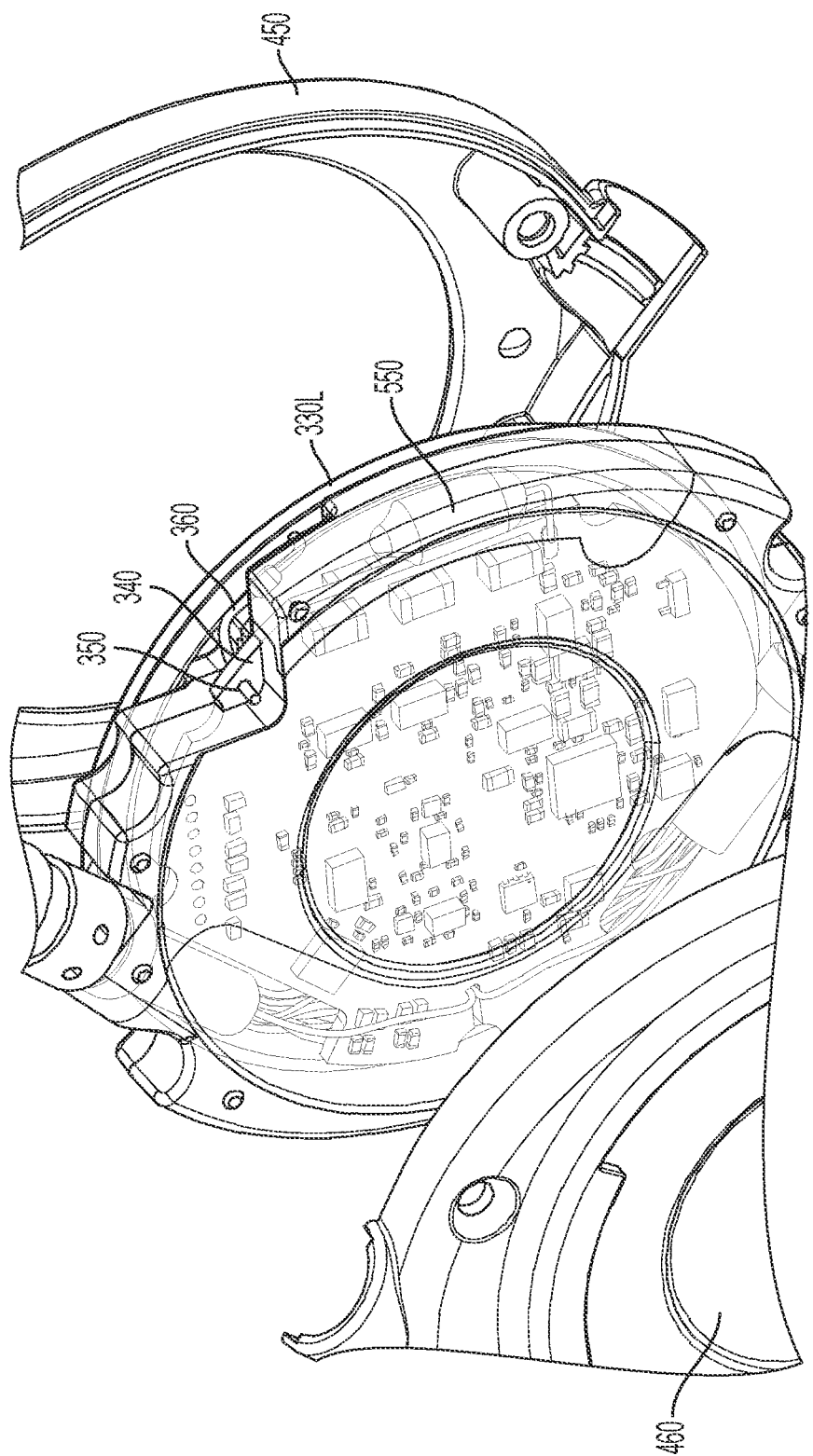
FIG. 5 is an exploded view of portions of an example of a water-resistant ECG electrode assembly.
Figure 8:
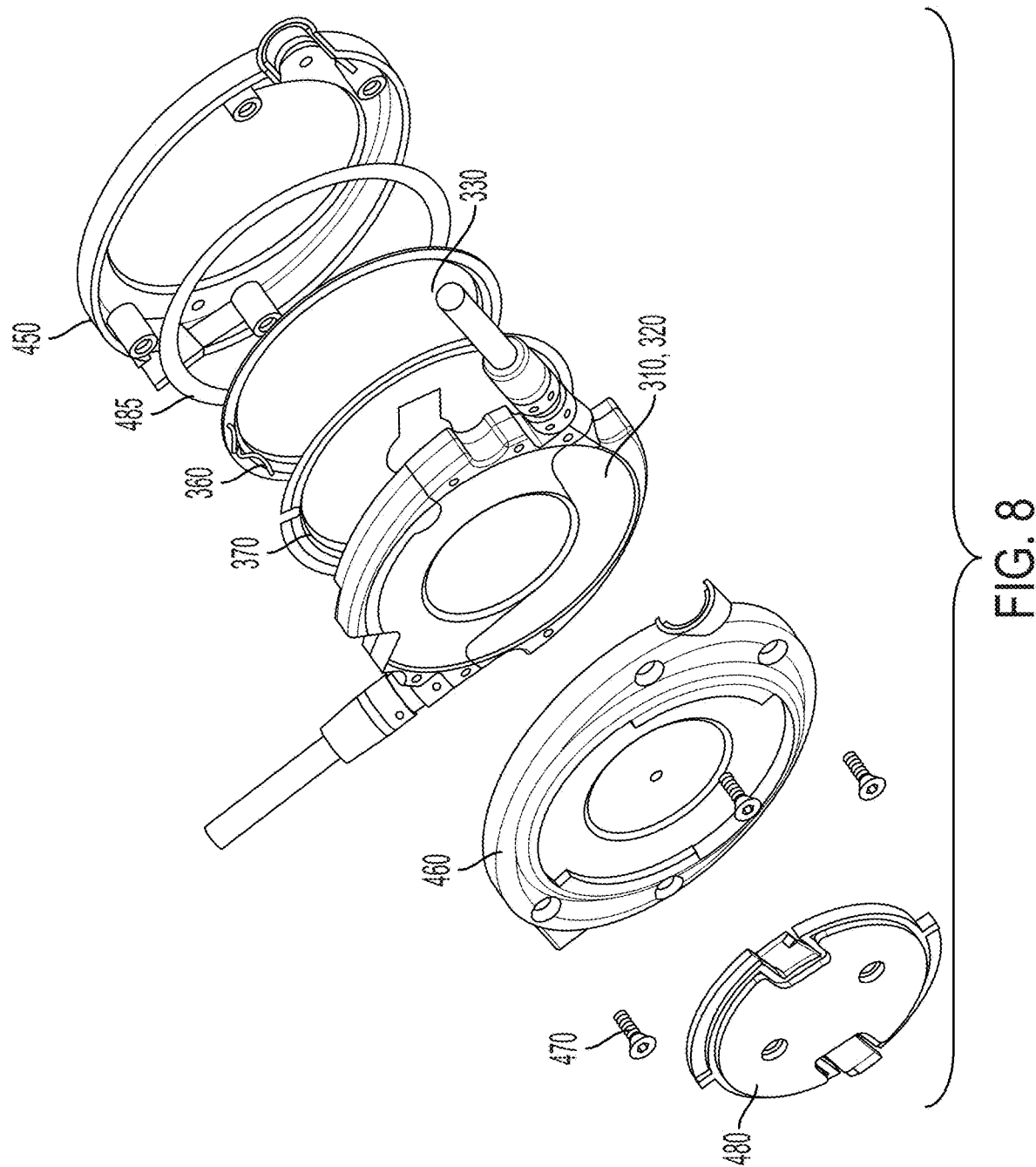
FIG. 8 is an exploded view of portions of an example of a water-resistant ECG electrode assembly.
Figure 9:
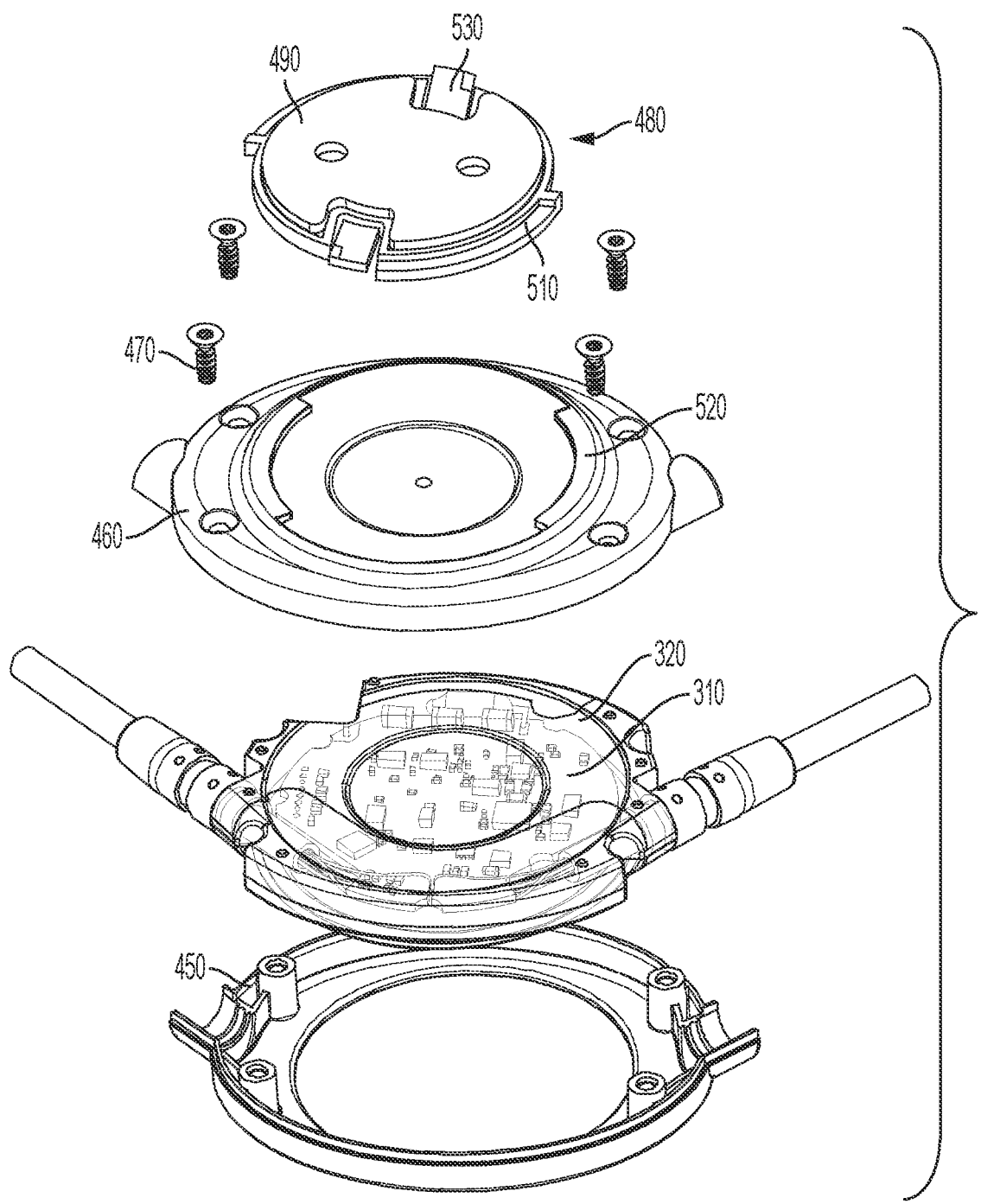
FIG. 9 is an exploded view of portions of an example of a water-resistant ECG electrode assembly.
Figure 10:
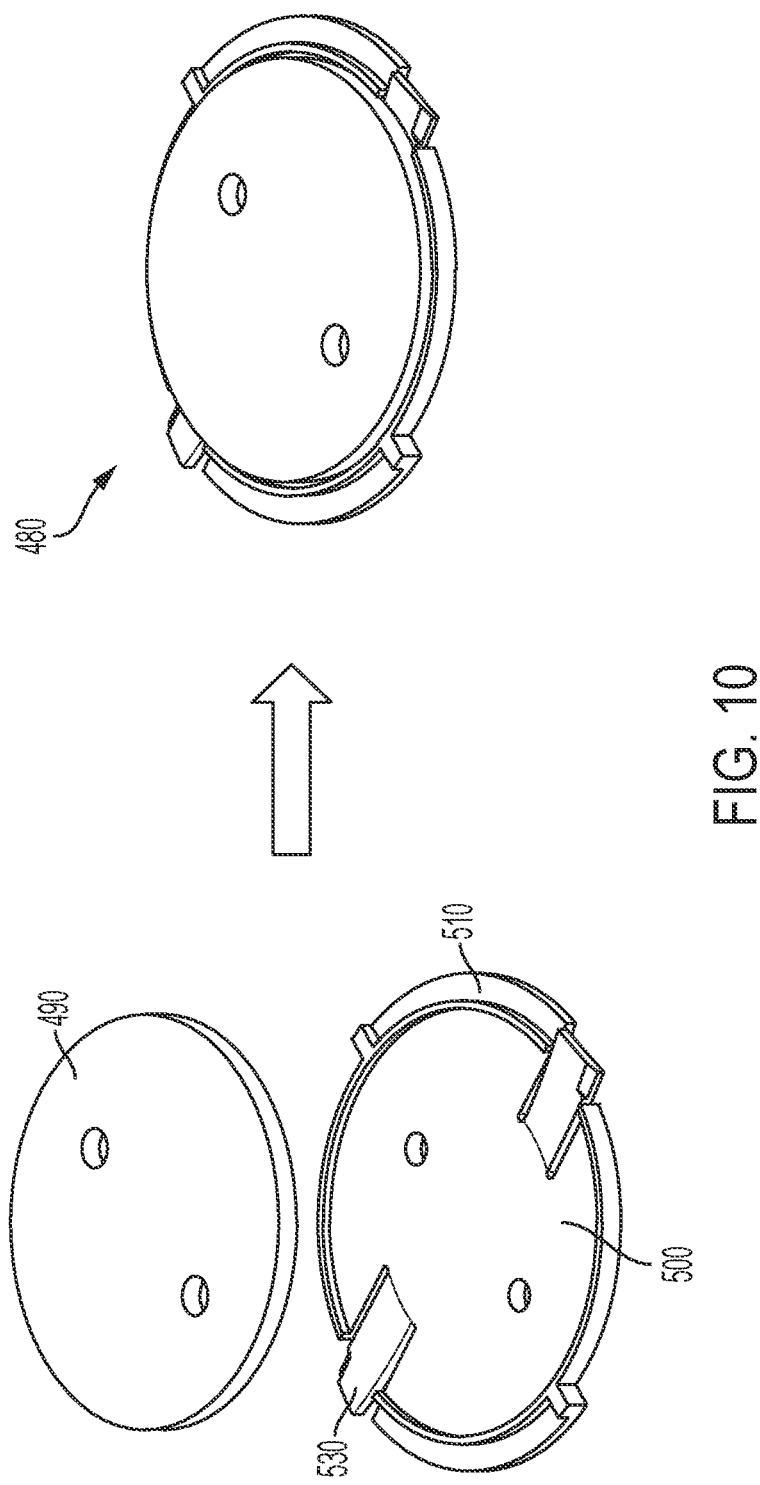
FIG. 10 illustrates an example of a mounting pad of an example of a water-resistant ECG electrode assembly.

Examples of the electrode assembly 300 may further include a housing including an upper shell 450 and a lower shell 460, for example, as illustrated in FIGS. 5, 6, 8, and 9. The housing encloses the main circuit board 310 and the main waterproof moldable dielectric polymer 320 and includes an aperture defined in the upper shell 450 to allow a raised central region 330U (illustrated in FIG. 3) of the ECG electrode 330 to extend through the upper shell 450 to contact the skin of a subject. The ECG electrode 330 may include a lowered peripheral region 330L (also illustrated in FIG. 3) that may be disposed between the upper shell 450 and the main waterproof moldable dielectric polymer 320 (and electrical insulator 370, when present) to help secure the ECG electrode 330 in place on the main waterproof moldable dielectric polymer 320. The upper shell 450 may be releasably secured to the lower shell 460 with one or more fasteners 470, for example, screws, bolts, snap fittings, or other appropriate fasteners known in the art. In some examples, a sealing gasket 485 may be provided between the lowered peripheral region 330L of the ECG electrode 330 and an internal portion of the upper shell 450. The electrical conductor 360 may be mechanically and electrically connected to the ECG electrode 330 at the lowered peripheral region 330L, for example, as illustrated in FIGS. 5, 6, and 8.

Figure 11A:
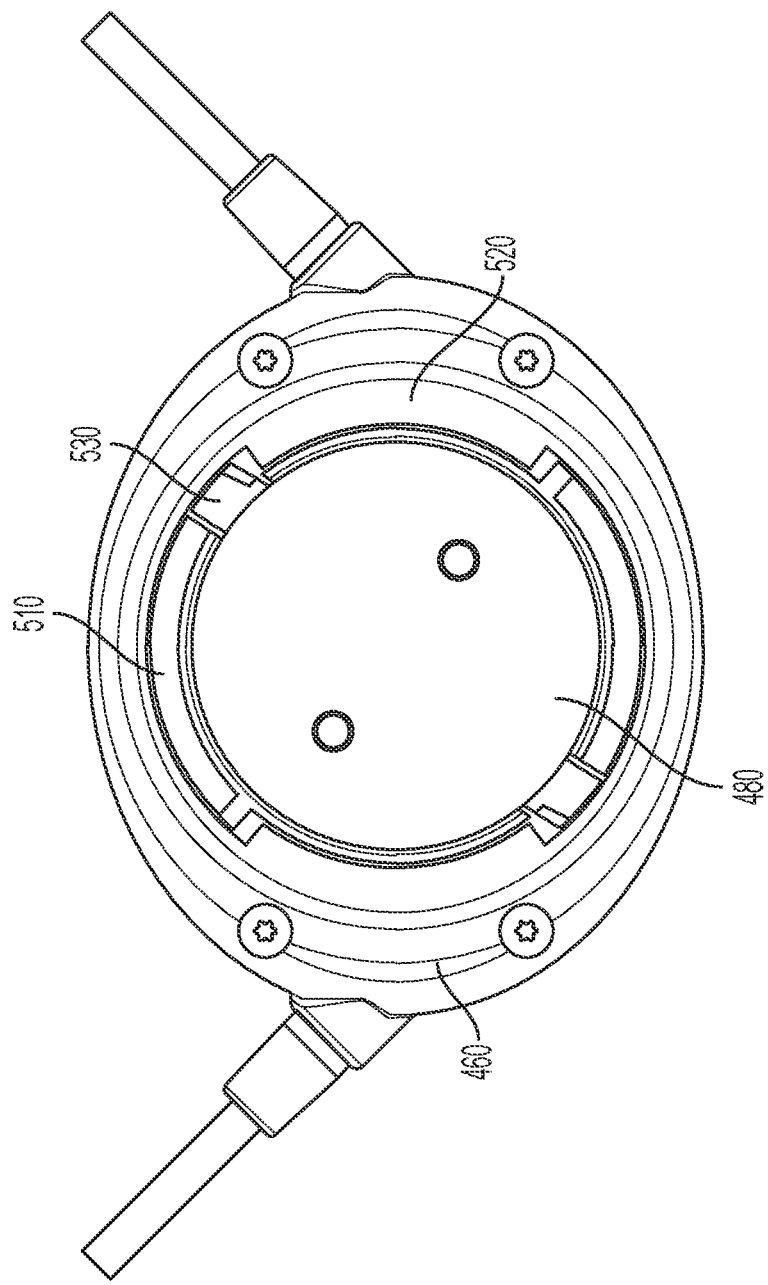
FIG. 11A illustrates the mounting pad of FIG. 10 in an unlocked configuration in a shell of an example of a water-resistant ECG electrode assembly.
Figure 11B:
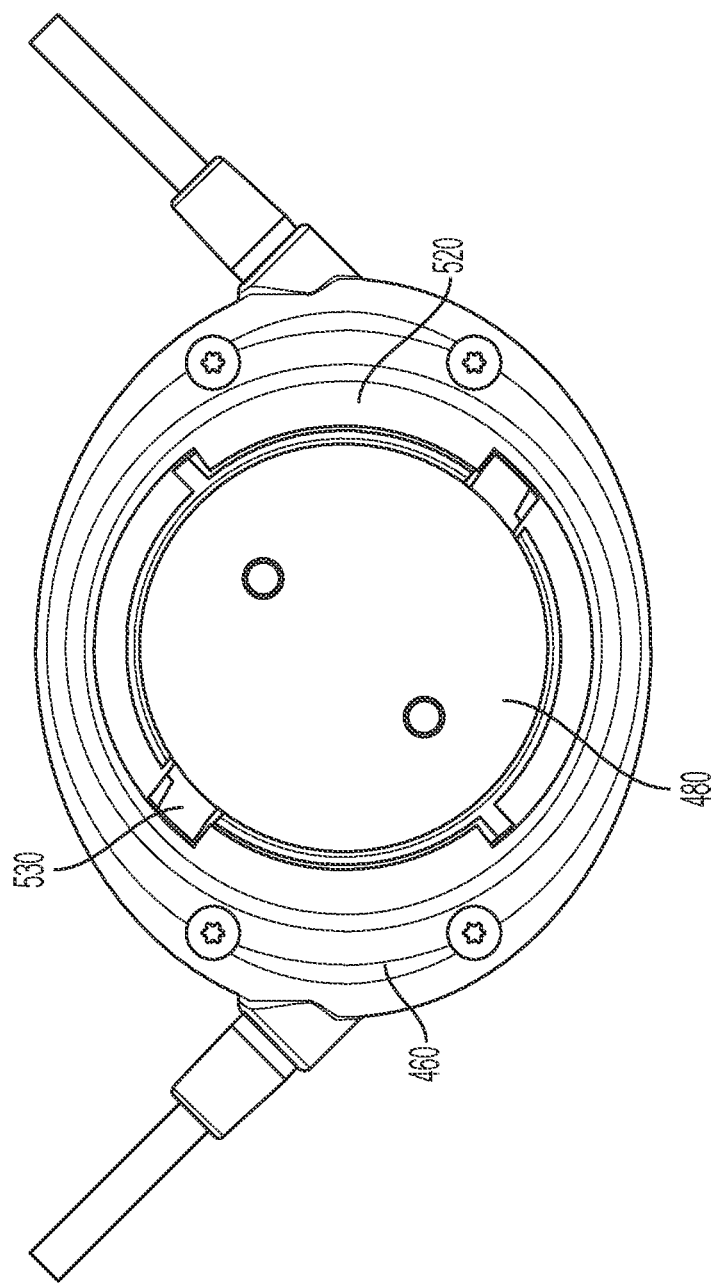
FIG. 11B illustrates the mounting pad of FIG. 10 in a locked configuration in a shell of an example of a water-resistant ECG electrode assembly.

Examples of the ECG electrode assembly 300 may further include a mounting pad 480, illustrated in FIGS. 6 and 8-11B, that may be used to removably secure the ECG electrode assembly within a wearable medical device 100 in which the ECG electrode assembly 300 is installed, for example, to a complimentary mounting patch disposed within the garment 110. The mounting pad 480 may include a hook pad 490 disposed on or adhesively coupled to a base 500. The hook pad 490 may include hooks configured to removably secure the ECG electrode assembly 300 within a garment 110 of the wearable cardiac monitoring device 100 by engaging complementary loop fasteners disposed in the garment 110. In other examples, the hook fasteners may be present in the garment 110 and the complimentary loop fasteners disposed on the hook pad 490. The base 500 may be removably rotatably securable to the lower shell 460 and may include retention flanges 510 that, when the mounting pad is rotated into place on the lower shell 460, fit beneath "portico" features 520 molded into the back of the lower shell 460, illustrated in FIGS. 9, 11A, and 11B. The base 500 may also include one or more locking tabs 530 which snap upward into areas between the "portico" features 520 of the lower shell 460 to prevent the mounting pad 480 from being rotated and removed from the lower shell unless the locking tabs 530 are depressed. FIG. 11A illustrates the mounting pad 480 placed in the lower shell 460 in an unlocked position and FIG. 11B illustrates the mounting pad 480 rotated into a locked position in the lower shell 460.

Figure 12:
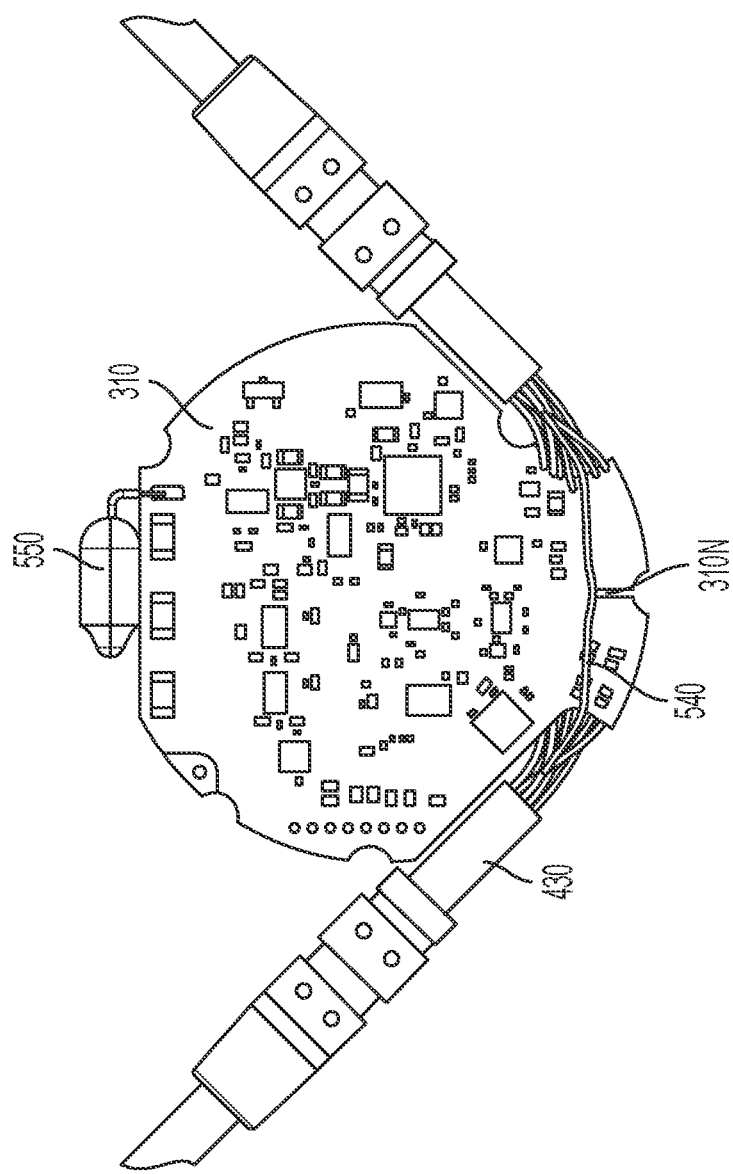
FIG. 12 depicts an example of a first, main circuit board assembly and associated tensile anchoring restraints and electrical connections for an ECG electrode assembly.

In some examples, in addition to electrically conductive wiring 420, the waterproof cables 430 may carry tensile anchoring restraints 540. The tensile anchoring restraints 540 may be high tensile strength non-conductive fibers, for example, aramid fibers such as DuPont™ Kevlar® para-aramid fibers. As illustrated in FIG. 12, the tensile anchoring restraints 540 extend out from inside of ends of the waterproof cables 430 and are mechanically coupled to the main circuit board 310, for example, adhesively secured in a slot or notch 310N in the main circuit board 310. The tensile anchoring restraints 540 anchor the waterproof cables 430 to the main circuit board 310 to increase an amount of force that might be required to pull the waterproof cables 430 out of the main waterproof moldable dielectric polymer 320 and break the electrical connection between the wiring 420 and the contacts on the main circuit board 310. The tensile anchoring restraints may enable the wiring 420 to withstand between about 15 pounds and about 100 pounds of tension without separating from the main circuit board 310, or from the interface circuit board 390 in examples including an interface circuit board 390 for wiring connections.

In some examples, the ECG electrode assembly 300 further includes a circuit protector, for example, a gas discharge tube 550. The gas discharge tube 550 can be electrically coupled to the main circuit board 310 within the main waterproof moldable dielectric polymer 320. The circuit protector, e.g., gas discharge tube 550, is configured to protect the active circuitry in the main circuit board 510 from electrical damage from a defibrillation shock delivered to a person wearing a wearable defibrillator 100 in which the ECG electrode assembly 300 is installed.

In some examples, the main waterproof moldable dielectric polymer 320 and interface circuit waterproof moldable dielectric polymer 400, when present, provides liquid ingress protection rating of at least one of IPX3, IPX4, IPX5, IPX6, IPX7, or IPX8 as specified in international standard IEC 60529 (British BS EN 60529:1992, European EN 60529:1989). These ingress protection ratings are defined as follows:

| Rating | Brief Description | Definition |
| --- | --- | --- |
| IPX3 | Protected against spraying water | Water sprayed at an angle up to 60° on either side of the vertical shall have no harmful effects. |
| IPX4 | Protected against splashing water | Water splashed against the enclosure from any direction shall have no harmful effects |
| IPX5 | Protected against water jets | Water projected in jets against the enclosure from any direction shall have no harmful effects |
| IPX6 | Protected against powerful water jets | Water projected in powerful jets against the enclosure from any direction shall have no harmful effects |
| IPX7 | Protected against the effects of temporary immersion in water | Ingress of water in quantities causing harmful effects shall not be possible when the enclosure is temporarily immersed in water under standardized conditions of pressure and time |
| IPX8 | Protected against the effects of continuous immersion in water | Ingress of water in quantities causing harmful effects shall not be possible when the enclosure is continuously immersed in water under conditions which shall be agreed between manufacturer and user but which are more severe than for numeral 7 |

The main waterproof moldable dielectric polymer 320 and interface circuit waterproof moldable dielectric polymer 400, when present, may also provide solid particle ingress protection rating of one of IP3X, IP4X, IP5X, or IP6X as specified in international standard IEC 60529 (British BS EN 60529:1992, European EN 60529:1989). These ingress protection ratings are defined as follows:

| Rating | Brief Description | Definition |
| --- | --- | --- |
| IP3X | Protected against solid foreign objects of 2.5 mm diameter and greater | The object probe, sphere of 2.5 mm diameter shall not penetrate at all |
| IP4X | Protected against solid foreign objects of 1.0 mm diameter and greater | The object probe, sphere of 1.0 mm diameter shall not penetrate at all |
| IP5X | Dust-protected | Ingress of dust is not totally prevented, but dust shall not penetrate in a quantity to interfere with satisfactory operation of the apparatus or to impair safety |
| IP6X | Dust-tight | No ingress of dust. |

Example implementations as described herein include the main or interface circuit boards, and associated electronics being encapsulated in moldable dielectric polymer. In some examples, encapsulation can be accomplished by pouring liquid polymer over electrical and electronic components, circuit boards and completed electronic assemblies for electrical insulation, waterproofing in accordance with the principles herein, and/or to protect the product against thermal shock, vibration, and corrosive substances. For example, encapsulation of the circuit boards into a moldable polymer compound can give environmental protection against water ingress and corrosion due to moisture in the air or caustic chemicals and gasses (e.g., sulfur may attack copper used in the components and circuit board tracks). Encapsulation also gives protection against the effects of mechanical shock and vibration, supporting and cushioning delicate or fragile components such as ferrites used in transformer cores. In examples, the encapsulation as described herein supports and takes much of the strain away from the circuit board pins, so that the strength of the pin connection to the circuit board is not reliant only on the solder joints. The encapsulation can also replace air around the circuit board with an insulating medium, thereby avoiding arc-over within power supplies with over-voltage stresses, including at high altitudes, and the effects of pollution such as moisture, dust and dirt which could reduce the insulation between the circuit board elements, or allow tracking to occur across surfaces. In examples, the moldable dielectric polymer can be configured to level-out thermal gradients, thus reducing temperature-difference stress on the circuit board components. In examples, the moldable dielectric polymer is configured to offer fire protection (e.g., UL94-V0 rated in accordance with the Standard for Safety of Flammability of Plastic Materials for Parts in Devices and Appliances testing) because once cured, the compound is configured to not ignite or maintain a flame.

In examples, the moldable dielectric polymer comprises polyamide hot melt material. In examples, the encapsulation process includes a low pressure molding with sealing adhesion and temperature and solvent resistance. The polymer encapsulates exposed circuitry to form the outer shell of the device and delivers a self-contained integrated assembly. Low application pressure between 20 and 500 psi within the mold cavity safeguards sensitive circuitry. When in a liquid state, the polymer flows in and around the dimensions of the circuit board without high levels of pressure (e.g., in excess of 500 psi) used with traditional injection molding or potting techniques. In this regard, the polymer can reduce stress even for miniaturized circuit components within the main and/or interface circuit boards. The polymer cycle time is very short, allowing for a high throughput process. Examples of such polymers and associated low pressure molding techniques are those of low-pressure molding techniques based on TECHNOMELT® from Henkel AG & Co. KGaA of Dusseldorf, Germany.

In examples, low pressure molding can be based on the following method. It is understood that this process is for illustration only and should not be used to limit the claims. For example, modifications or deviations from the below process are possible, and such modifications or deviations may be within the spirit and scope of the present disclosure. For example, the polymer material is heated until liquid (e.g., at 356° to 464° Fahrenheit/180° to 240° Celsius) and then injected at very low pressure, typically 20 to 500 psi, into a relatively cold mold-set. The low viscosity polymer material flows into the mold-set cavity and around the electronics to be encapsulated. The polymer starts cooling down as soon as it touches the mold-set cavity and the electronics. A mold-set cavity is filled in seconds, e.g., a full molding cycle can be between 20 to 45 seconds. As the polymer material starts to cool down it also starts to shrink. In some processes, continuous injection pressure is therefore applied to the cavity, even after its initial fill. This can be done to compensate for the shrinkage that naturally occurs when the polymer material goes from liquid to solid (e.g., hot to cold). The polymer temperature is not too hot for the electronics and does not re-melt or re-flow the solder. The relatively cold mold-set can absorb the brunt of the heat, thereby reducing the temperature to which the circuit board and associated electronics are exposed. Such low injection pressure does not stress solder joints.

In examples, encapsulation may be accomplished by a potting process. In this process, the circuit board and/or associated electronics are placed inside a mold which is then filled with the dielectric polymer material, an insulating liquid compound that hardens, permanently protecting the circuit board. The mold may provide shielding or heat dissipating functions in addition to acting as a mold. Accordingly, when the mold is removed the potted assembly is described as being cast.

In examples, encapsulation may be accomplished by conformal coating. For example, the circuit boards and associated electronics are coated with a layer of conformal coating based on the polymer material. Conformal coating gives most of the benefits of potting, and is lighter and easier to inspect, test, and repair. In examples, conformal coatings can be applied as liquid or condensed from a vapor phase.

In examples, encapsulation may be accomplished by dipping the circuit board and/or associated electronics in a liquid form of the polymer material. For example, the circuit boards and associated electronics are dipped so that they are covered with a layer of coating based on the polymer material.

Although the subject matter contained herein has been described in detail for the purpose of illustration, it is to be understood that such detail is solely for that purpose and that the present disclosure is not limited to the disclosed examples, but, on the contrary, is intended to cover modifications and equivalent arrangements that are within the spirit and scope of the appended claims. For example, it is to be understood that the present disclosure contemplates that, to the extent possible, one or more features of any example can be combined with one or more features of any other example.

Other examples are within the scope and spirit of the description and claims. Additionally, certain functions described above can be implemented using software, hardware, firmware, hardwiring, or combinations of any of these. Features implementing functions can also be physically located at various positions, including being distributed such that portions of functions are implemented at different physical locations.

What is claimed is:
1. A waterproof modular electrocardiogram (ECG) electrode assembly for use in a wearable cardiac monitoring device, the assembly comprising:
　a main circuit board comprising active ECG processing circuitry encapsulated in a main circuit waterproof moldable dielectric polymer; and
　an ECG electrode mechanically coupled to the main circuit waterproof moldable dielectric polymer, the ECG electrode configured to be electrically coupled to a portion of the main circuit board;
　wherein the ECG electrode is removably coupled to the main circuit waterproof moldable dielectric polymer with an adhesive; and
　wherein an insulating material layer is disposed between the ECG electrode and the main circuit waterproof moldable dielectric polymer.
2. The assembly of claim 1, wherein the portion of the main circuit board is configured to extend outside of the main circuit waterproof moldable dielectric polymer.

3. The assembly of claim 1, wherein the ECG electrode is removably electrically coupled to the main circuit board.

4. The assembly of claim 1, further comprising an interface circuit board and an interface circuit waterproof moldable dielectric polymer, wherein the interface circuit board is potted in the interface circuit waterproof moldable dielectric polymer and wherein the interface circuit board is removably electrically and mechanically coupled to the main circuit board.

5. The assembly of claim 4, further comprising a dielectric sealing compound disposed between the main circuit board and the interface circuit board, the dielectric sealing compound including a dielectric grease disposed about an electrical connection between the main circuit board and the interface circuit board.

6. The assembly of claim 1, further comprising a housing including an upper shell and a lower shell, the upper shell being removably coupled to the lower shell, a perimeter of the ECG electrode disposed between the upper shell and the main circuit waterproof moldable dielectric polymer.

7. The assembly of claim 6, further comprising a base that is removably rotatably securable to the lower shell, the assembly further comprising a mounting pad including a hook pad that is disposed on the base, the hook pad configured to removably secure the assembly within a garment of the wearable cardiac monitoring device by engaging complementary fasteners disposed in the garment.

8. The assembly of claim 7, wherein:
the lower shell includes first and second portico features and a slot defined between the first and second portico features;
the base includes a retention flange configured to slide under at least one of the first and second portico features of the lower shell; and
the base includes a locking tab configured to removably engage the slot and secure the mounting pad in place in the lower shell.

9. The assembly of claim 6, wherein the main circuit board and the main circuit waterproof moldable dielectric polymer are disposed within the housing.

10. The assembly of claim 6, wherein the ECG electrode includes a raised central region and a lowered peripheral region, the lowered peripheral region configured to be disposed between the upper shell and the main circuit waterproof moldable dielectric polymer.

11. The assembly of claim 10, wherein the portion of the main circuit board is configured to extend outside of the main circuit waterproof moldable dielectric polymer, the assembly further comprising a conductor electrically coupling the ECG electrode to the portion of the main circuit board extending outside of the main circuit waterproof moldable dielectric polymer, the conductor being electrically and mechanically coupled to the ECG electrode at the lowered peripheral region.

12. The assembly of claim 1, further comprising wiring electrically connected to the main circuit board within the main circuit waterproof moldable dielectric polymer, the wiring being enclosed in a waterproof cable including a flex relief connector extending outward from an interface between the waterproof cable and the main circuit waterproof moldable dielectric polymer, a tensile anchoring restraint extending from inside the waterproof cable and mechanically coupled to the main circuit board.

13. The assembly of claim 12, wherein the tensile anchoring restraint comprises a non-conductive fiber that enables the wiring to withstand between about 15 pounds and about 100 pounds of tension without separating from the main circuit board.

14. The assembly of claim 1, further comprising a circuit protector electrically coupled to the main circuit board within the main circuit waterproof moldable dielectric polymer and configured to protect the active ECG processing circuitry from electrical damage from a defibrillation shock delivered to a person wearing the wearable cardiac monitoring device.

15. The assembly of claim 1, wherein the main circuit waterproof moldable dielectric polymer provides liquid ingress protection rating of at least one of IPX3, IPX4, IPX5, IPX6, IPX7, or IPX8 as specified in international standard IEC 60529 (British BS EN 60529:1992, European EN 60529:1989).

16. The assembly of claim 15, wherein the main circuit waterproof moldable dielectric polymer provides solid particle ingress protection rating of one of IP3X, IP4X, IP5X, or IP6X as specified in international standard IEC 60529 (British BS EN 60529:1992, European EN 60529:1989).

17. The assembly of claim 1, wherein the assembly is removably disposable within a garment of the wearable cardiac monitoring device.

18. The assembly of claim 1, wherein the assembly includes a portion that is permanently disposed within a garment of the wearable cardiac monitoring device, the portion of the assembly including an interface circuit board potted in an interface circuit waterproof moldable dielectric polymer and removably electrically and mechanically coupled to the main circuit board.

19. The assembly of claim 1, wherein the wearable cardiac monitoring device comprises a wearable cardioverter defibrillator.

* * * * *